United States Patent [19]

Romano et al.

[11] Patent Number: 4,514,339

[45] Date of Patent: Apr. 30, 1985

[54] PROCESS FOR PREPARING ALKYL ISOCYANATES

[75] Inventors: Ugo Romano, Vimercate; Franco Rivetti, Schio; Giacomo Sasselli, S. Donato Milanese, all of Italy

[73] Assignee: Enichimica S.p.A., Milan, Italy

[21] Appl. No.: 608,984

[22] Filed: May 10, 1984

[30] Foreign Application Priority Data

May 13, 1983 [IT] Italy .............................. 21081 A/83

[51] Int. Cl.³ .............................................. C07C 69/00
[52] U.S. Cl. ................................................ 260/453 P
[58] Field of Search ...................... 260/453 P, 453 AL

[56] References Cited

U.S. PATENT DOCUMENTS 2,409,712 10/1946 Schweitzer ...................... 260/453 P
3,366,662 1/1968 Kober et al. ..................... 260/453 P
3,919,278 11/1975 Rosenthal et al. ............... 260/453 P Primary Examiner—Alan Siegel
Attorney, Agent, or Firm—Hedman, Gibson, Costigan & Hoare

[57] ABSTRACT

Process for the production of alkyl isocyanates which can be defined by the general formula: $R-N=C=O$ wherein R is an alkyl radical having from 1 to 4 carbon atoms by thermal decomposition of phenyl-N-alkyl urethans which can be defined by the general formula:

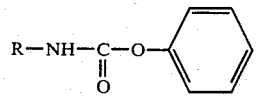

wherein R has the above defined meaning. Said thermal decomposition is carried out without any substance having a catalytic activity being present in the decomposition reaction, by heating to a temperature of from 180° C. to 210° C. under the atmospherical pressure or a slightly reduced pressure, a mixture of phenol and phenyl-N-alkyl urethan, in a molar ratio of the former to the latter equal to or nearly equal to 1:1, removing by vaporization the phenol and the alkyl isocyanate from said vaporized products and maintaining in the reaction mixture, substantially throughout the thermal decomposition a molar ratio of phenol to phenyl-N-alkyl urethan not lower than about 1:1.

5 Claims, 1 Drawing Figure

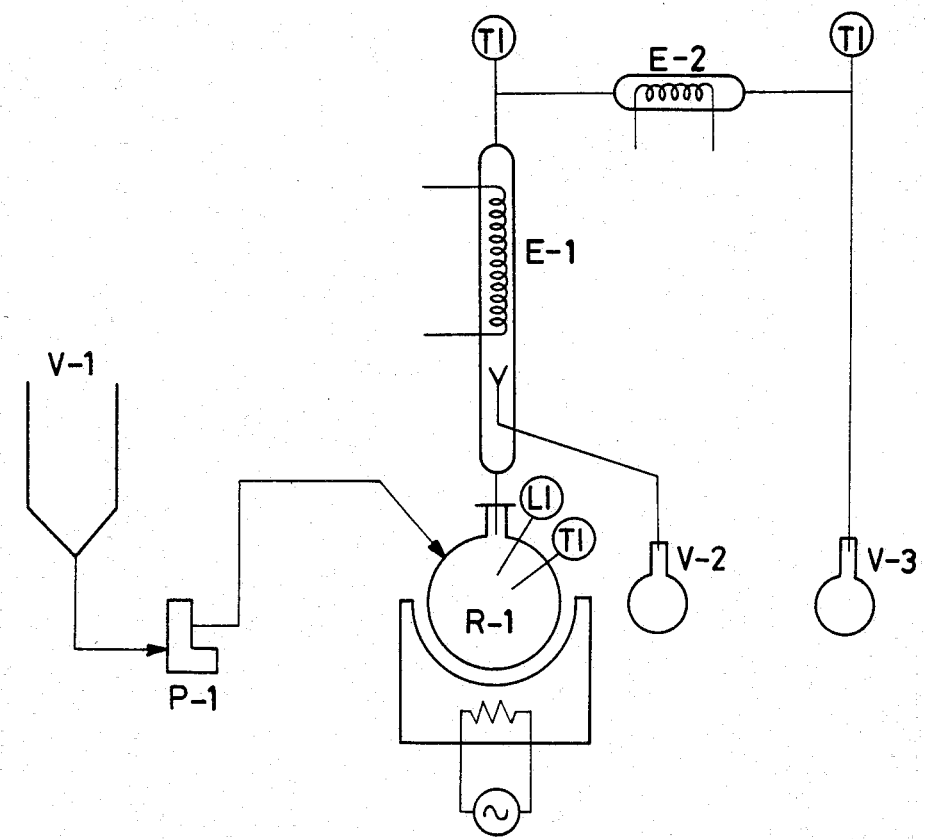

PROCESS FOR PREPARING ALKYL ISOCYANATES

The present invention relates to an improved process for the production of alkyl isocyanates, by thermal decomposition of the corresponding phenyl-N-alkyl urethans. Alkyl isocyanates in general, and methyl isocyanate in particular, are appreciable intermediates, which are particularly useful for the production of phytopharmaceutical such as for example those known in the trade under the name Carbofuran (2,3-dihydro-2,2-dimethylbenzofuran-7-yl-methylcarbamate), Carbaryl (1-naphthyl-methylcarbamate), Propoxur (2-isopropoxyphenyl-N-methylcarbamate) and Benthiocarb (S-(4-chlorobenzyl)-N,N-diethylthiocarbamate).

Known in the art are processes for the preparation of isocyanates by reaction of phosgene with an amine, in this connection, please refer to Kirk-Othmer, "Encyclopedia of Chemical Technology", 3rd Edition, Vol. 13 (1982), pages 789 and seqq. These procedures are particularly suitable for the production of the higher-boiling aliphatic isocyanates, of the aromatic isocyanates and of the diisocyanate, whereas they are poorly adapted to the synthesis of the lower boiling aliphatic isocyanates and this, above all, due to their more pronounced reactivity, which is very likely conducive to side reactions, such as trimerization, and reactions leading to the formation of ureas and others. Moreover, such known processes exhibit the hazards deriving from the use of a highly toxic reactant such as phosgene.

Therefore, there have been suggested in the art other processes for producing the isocyanates by excluding the use of phosgene, these processes being based, essentially, on the pyrolysis of alkyl- or aryl urethans, such as disclosed for example in "Annalen der Chemie, 562, 205 (1949) and in "Methoden der Organischen Chemie", Vol. 8, page 126 (1952).

More particularly, according to such known processes, the aliphatic or the aromatic urethans are subjected to pyrolysis at a high temperature, to produce the corresponding isocyanate along with an alcohol or phenol. However, in these pyrolytic processes carried out at a high temperature, the values of the conversion of the urethans and the selectivity of the useful reaction products, are heavily affected both by the preselected reactants and the conditions under which the pyrolysis is carried out. There is, on this subject matter, a comprehensive literature, especially patent literature, in which there are disclosed processes for the preparation of isocyanates, which are essentially based on the use of particular reactants, or of particular working conditions, or the use of solvents or other inert media for the pyrolysis or of particular substances having a catalytic influence on said pyrolysis. Cited in this connection are the U.S. Pat. Nos. 1,247,451; 3,076,007; 4,003,938 and 4,123,450; the German Patent Application No. 27 56 928 and the European Patent Publication No. 48 368. These processes, however, are not fully satisfactory, especially in view of the comparatively low values of the conversion of the urethans into the corresponding isocyanates. Said conversion values attain, typically, maximum percentages in the order of 90% and, moreover, the formation is experienced of by-products, such as those deriving from cyclotrimerization reactions, condensations and others, which originates the loss of useful products and which often pollute the expected reaction product, so that purification runs are consequently required.

The objective of the present invention is to provide a process for the preparation of alkyl isocyanates by thermal decomposition of phenyl-N-alkyl urethans, which is deprived, or substantially so, of the above discussed shortcomings. The present invention is essentially based on the discovery that the thermal decomposition of the phenyl-N-alkyl urethans, admixed with at least equimolecular amounts of phenol, proceeds with unexpectedly high yield and selectivities, to give the corresponding alkyl isocyanate with a purity which is sufficient to dispense with any purification run. In accordance with the foregoing, the present invention relates to a process for the preparation of alkyl isocyanates which can be defined by the general formula R—N═C═O wherein R is an alkyl radical having from 1 to 4 carbon atoms, by thermal decomposition of phenyl-N-alkyl urethans which can be defined by the general formula:

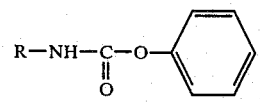

wherein R has the above defined meaning, whereby said decomposition is carried out in the absence of any substances having any catalytic action on the decomposition reaction, by heating to a temperature of from 180° C. to 210° C. and under the atmospherical pressure or a slightly reduced pressure, a mixture of phenol and phenyl-N-alkyl urethan, in a molar ratio of the former to the latter equal to about 1:1, withdrawing by vaporization both the phenol and the alkyl isocyanate as they are being formed, recovering the alkyl isocyanate from said vaporized products and maintaining in the reaction mixture, substantially along the entire duration of the thermal decomposition, a molar ratio of phenol to phenyl-N-alkyl urethan not lower than about 1:1.

The phenyl-N-alkyl urethans which are useful to the purposes of the present invention are those which can be defined by the above reported general formula, in which R is a radical such as methyl, ethyl, n. propyl, isopropyl, n. butyl, isobutyl and tert.butyl.

According to the process of the present invention, an equimolecular, or nearly so, mixture of phenol and a phenyl-N-alkyl urethan is prepared, and this mixture is heated to a temperature in the range from 180° C. to 210° C. to bring about the thermal decomposition of the phenyl-N-alkyl urethan into phenol and alkyl isocyanate. Said decomposition is carried out under the atmospherical pressure or under a reduced pressure, for example between 760 mmHg and 200 mmHg. Lower pressures can be adopted, but they are undesirable, as a rule.

According to an embodiment of the process according to the present invention, the decomposition of the phenyl-N-alkyl urethan is carried out without any inert solvent being present and also without any substances as known in the art as having a catalytic influence upon the decomposition reactions. In addition, the temperature and pressure conditions are such as to remove by vaporization, from the reaction environment, both the phenol and the alkyl isocyanate as they are being formed.

A fundamental aspect of the process of the present invention is that of maintaining, in the reaction environment and substantially along the entire duration of the decomposition, a molar ratio of the phenol to the phenyl-N-alkyl urethan to values of not less than about 1:1. The best results, in terms of yields and selectivity of the reaction, are obtained with values of said ratio equal to or nearly equal to 1:1.

In the latter case, in the course of the decomposition, a mixture is vaporized, which is composed of about two molecules of phenol per each molecule of alkyl isocyanate. There can be adopted values of the ratio above 1:1 and up to about 3:1 and useful results can still be obtained. Higher ratios are undesirable as they originate a lowering of the yield and the selectivity of the reaction.

At any rate, the phenol and the alkyl isocyanate are condensed separately from the products of the vaporization, and are recovered.

When working under the conditions disclosed in the foregoing, there are obtained values of conversion of the phenyl-N-methyl urethan over about 97 molar%, with a selectivity for the alkyl isocyanate higher than 97 molar% relative to the converted urethan. It is possible, moreover, to obtain the alkyl isocyanate with a purity higher than about 99%.

The process of the present invention can be carried out as a batch-process, or it can be performed in a continuous run by feeding the reaction environment, maintained under the decomposition conditions, with an equimolecular mixture of phenyl-N-methyl-urethan and phenol.

The ensuing practical examples illustrate the invention without limiting same.

EXAMPLE 1 (A comparative example)

A glass flask, having at its top a reflux condenser thermostatically controlled at 70° C., is charged with 75.5 g (0.50 mol) of phenyl-N-methyl urethan, working under a nitrogen blanket. The reactant is heated to 200° C. so that the decomposition of the phenyl-N-methyl urethan is started whereby methyl isocyanate and phenol are set free.

On account of the temperature in the condenser, phenol is refluxed whereas methyl isocyanate is distilled out and is subsequently condensed within a cold trap.

After 6 hours, the temperature drops to 182° C. and the reaction stops.

There are collected 19.6 g (0.344 mol) of methyl isocyanate in the cold trap.

There are left in the reaction flask 55.9 g of a mixture of phenol (33 g), phenyl-N-methyl urethan (19.6 g) and other unidentified products (3.3 g). Thus, the conversion of the phenyl-N-methyl urethan is as low as 74%, with a selectivity of methyl isocyanate of 93% relative to the converted urethan, said percentages being expressed on a molar basis. The purity of the isocyanate so obtained is 99.8%.

EXAMPLE 2

A glass flask is used, which is heated on a thermostatically controlled oil bath and is equipped with a magnetic stirrer, a thermometer and a nitrogen inlet. The flask is topped by a distillation device for the collection of phenol, with a condenser heated to 70° C. A subsequent cold trap is intended for collecting the methyl isocyanate. The flask is charged with 56.47 g (0.374 mol) of phenyl-N-methyl urethan and 35.16 g (0.374 mol) of phenol. The temperature is raised to 198° C. under a nitrogen blanket, the reaction mass being stirred. There are vaporized from the flask phenol and methyl isocyanate in a molar ratio of former to the latter equal to about 2:1, while maintaining the temperature in the flask to the preselected value. The reaction is completed after about 6 hours. There are collected in the cold trap 20.86 g. (0.366 mol) of methyl isocyanate. In the phenol trap there are recovered 63.7 g of a mixture of phenol (63.05 g; 98.9%) and of phenyl-N-methyl urethan (0.67 g; 1.05%).

A residue is left in the reaction flask which weighs 7.1 g and consists of phenol (6.77 g; 95.3%), phenyl-N-methyl urethan (0.12 g; 1.7%) and other unidentified nitrogenous compounds (0.2 g).

Thus the conversion of phenyl-N-methyl urethan is 98.6%, with a selectivity of methyl isocyanate equal to 99.3% with respect to the converted urethan, the percentages being expressed on a molar basis. The recovery of phenol is virtually complete. The purity of the isocyanate thus obtained is 99.8%.

EXAMPLE 3

The procedure is akin to that of the previous Example and the flask is charged with 35.8 g (0.2 mol) of phenyl-N-n. propyl urethan and 18.8 g (0.2 mol) of phenol. The reaction is carried out during 6 hours approximately at 200° C. As this period of time has elapsed, there are collected 16.5 g (0.194 mol) of n. propyl isocyanate having a boiling point of 88° C., and 33.1 g (0.352 mol) of phenol. A residue (5.0 g) is left in the flask and consists of phenol (3.9 g), phenyl-N-n.propylurethan (0.9 g) and other unidentified nitrogenous compounds (0.2 g).

Thus, the conversion of the phenyl-N-n.propyl urethan is as much as 97.4%, with a selectivity of n. propyl isocyanate equal to 99.5% with respect to the converted urethan. The percentages being expressed on a molar basis.

The recovery of phenol is virtually complete. The purity of the isocyanate thus obtained is 99%.

EXAMPLE 4

This Example illustrates the preparation of methyl isocyanate from phenyl-N-methyl urethan in a continuous run.

Having now reference to FIG. 1, the reactor R-1 is a 1-liter glass flask heated by an oil bath and having a magnetic anchor stirrer, and equipped with an external level gauge, the flask being maintained under a very slight pressure (10 to 20 mmH$_2$O) of nitrogen. The reactor R-1 is charged with 700 g of a solution which contains 278 g (2.957 mols) of phenol and 442 g (2.794 mol) of phenyl-N-methyl urethan.

The temperature in R-1 is slowly raised to 193° C.-194° C. and maintained at such values by adjusting the oil bath temperature.

Under these conditions, the thermal decomposition of the phenyl-N-methyl urethan occurs, accompanied by the gradual vaporization of the products of the reaction decomposition (methyl isocyanate and phenol) and also of the added phenol. The vertical condenser E-1 which is water cooled at 70° C., provides partially to condensate the vapors, thus separating phenol from methyl isocyanate and phenol is collected in a flask V-2. Methyl isocyanate is condensed with brine in E-2 and collected in V-3. As the reaction proceeds, the liquid level in R-1 tends to drop and the gear pump P-1 provides to continuously feed from V-1 into R-1 a mixture of phenyl-N-methyl urethan and phenol, having a composition equal to that of the initially fed mixture and in such a volume as to maintain a constant liquid level in R-1.

The symbols TI and LI indicate temperature and level controls. Under steady conditions, which are attained after about 4–5 hours, the situation is as follows:

Feeding to R-1:
phenyl-N-methyl urethan: 155 g/hour (1.026 mol/hour);
phenol: 102 g/hour (1.085 mol/hour);

collected at V-2:
phenol: 196 g/hour (2.085 mol/hour);
phenyl-N-methyl urethan: 3 g/hour (0.0198 mol/hour);

collected at V-3:
methyl isocyanate: 56 g/hour (0.982 mol/hour).

Under these conditions, there is experienced, as an average, under steady conditions, a conversion of phenyl-N-methyl urethan as high as 98%, with a selectivity of methyl isocyanate of 97.5% with respect to the converted urethan the percentages being expressed on a molar basis.

The potential output is about 80 Kg/hour of methyl isocyanate per cubic meter of useful volume of the reactor. The purity of the isocyanate is 99.8%.

On completion of the reaction, there have been found in the reactor R-1 small values of high-boiling, nitrogenous unidentified compounds.

We claim:

1. Process for the preparation of alkyl isocyanate which can be defined by the general formula R—N=C=O, wherein R is an alkyl radical having from 1 to 4 carbon atoms, by thermal decomposition of phenyl-N-alkyl urethans which can be defined by the general formula:

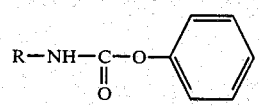

wherein R has the above defined meaning, characterized in that said thermal decomposition is carried out without using any substance having a catalytic action upon the decomposition reaction, by heating to a temperature of from 180° C. to 210° C. and under the atmospherical pressure or a slightly reduced pressure, a mixture of phenol and phenyl-N-alkyl urethan, in a molar ratio of the former to the latter equal to, or about equal to 1:1, removing by vaporization the phenol and the alkyl isocyanate as they are being formed, recovering the alkyl isocyanate from said vaporized products and maintaining in the reaction mixture, substantially during the entire thermal decomposition reaction time, a molar ratio of phenol to phenyl-N-alkyl urethan not lower than 1:1.

2. Process according to claim 1, characterized in that the thermal decomposition is carried out under a pressure of from 760 mmHg to 200 mmHg.

3. Process according to claim 1, characterized in that during the thermal decomposition reaction time there is maintained in the reaction mixture a molar ratio of phenol to phenyl-N-alkyl urethan of from 1:1 to 3:1.

4. Process according to claim 1, characterized in that during the thermal decomposition reaction time there is maintained in the mixture a molar ratio of phenol to phenyl-N-alkyl urethan equal to, or nearly equal to 1:1 and a gaseous mixture is vaporized, which contains about 2 mols of phenol per each mol of alkyl isocyanate.

5. Process according to claim 1, characterized in that it additionally comprises the fractional condensation of the phenol and the alkyl isocyanate from the vaporized products and the separate recovery of such compounds.

* * * * *